United States Patent
Shaw (10) Patent No.: US 6,511,798 B1
(45) Date of Patent: Jan. 28, 2003

(54) METHODS FOR THE PREPARATION OF CELL MONOLAYERS

(75) Inventor: Charles Michael Shaw, Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/268,695

(22) Filed: Mar. 16, 1999

(30) Foreign Application Priority Data

Mar. 17, 1998 (GB) ................................. 9805519

(51) Int. Cl.⁷ ..................... G01N 33/53; G01N 33/543; G01N 33/48; A01N 1/00; C12N 5/00
(52) U.S. Cl. ............................ 435/4; 435/1.1; 435/7.1; 435/7.21; 435/7.92; 435/30; 435/40.5; 435/40.51; 435/174; 435/176; 435/177; 435/178; 435/179; 435/180; 435/325; 435/366; 435/373; 435/374; 435/377; 435/383; 435/384; 435/385; 435/395; 435/401; 435/969; 436/518; 436/524; 436/528; 436/529
(58) Field of Search .................. 425/288; 435/284, 435/308.1, 347, 363, 373, 374, 261, 287.1, 287.9, 366, 375, 325, 4, 368, 370, 378, 383, 384, 369, 371, 377, 372, 40.5, 40.57, 818, 286.1, 181, 948, 180, 29, 34, 175, 245, 179, 283.1, 178, 177, 174, 70.1, 243, 244, 385, 386, 387, 388, 389, 390, 391, 392, 393, 394, 395, 396, 397, 398, 399, 400, 401, 402, 403, 404; 435/405, 406, 407, 408; 514/11, 12, 21; 530/317, 356; 436/518, 524, 528, 529

(56) References Cited

U.S. PATENT DOCUMENTS

| | | | | |
|---|---|---|---|---|
| 4,224,413 A | * | 9/1980 | Burbidge | 435/284 |
| 4,501,815 A | * | 2/1985 | Reid et al. | 435/284 |
| 5,219,752 A | * | 6/1993 | Takazawa et al. | 435/240.25 |
| 5,731,417 A | * | 3/1998 | Swiderek et al. | 530/356 |
| 5,856,189 A | * | 1/1999 | Watkins et al. | 435/375 |
| 6,022,733 A | * | 2/2000 | Tam et al. | 435/287.1 |

OTHER PUBLICATIONS

Takaku et al. An in vitro coculture model of transmigrant monocytes and foam cell formation. Arteriosclerosis Thrombosis and Vascular Biology. vol. 19, No. 10 (1999) pp. 2330–2339.*

Riley et al. Active hexose transport across cultured human CaCo–2 cells: characterisation and influence of culture conditions. Biochimica et Biophysica Acta. vol. 1066, No. 2 (1991) pp. 175–182.*

Yee. In vitro permeability across CaCo–2 cells (colonic) can predict in vivo (small intestinal) absorption in man–fact or myth. Pharmaceutical Research. vol. 14, No. 6 (1997) pp. 763–766.*

Hashimoto et al. Epithelial properties of human intestinal CaCo–2 cells cultured in a serum–free medium. Cytotechnology. vol. 13, No. 3 (1993) pp. 175–184.*

Mangum et al. Co–culture of primary pulmonary cells to model alveolar injury and translocation or proteins. In Vitro Cellular and Developmental Biology. vol. 26, No. 12 (1990) pp. 1135–1143.*

(List continued on next page.)

*Primary Examiner*—Long V. Le
*Assistant Examiner*—Kartic Padmanabhan
(74) *Attorney, Agent, or Firm*—Rothwell, Figg, Ernst & Manbeck (57) ABSTRACT

Cell based screens for studying drug transport are described and improved methods for the preparation of cell monolayers for use in such screens are disclosed.

8 Claims, 7 Drawing Sheets

OTHER PUBLICATIONS

Sergent–Engelen et al. Improved cultivation of polarized animal cells on culture inserts with new transparent polyethylene terephtalate or polycarbonate microporous membranes. Biotechnology Techniques. vol. 4, No. 2 (1990) pp. 89–94.*

Halleux et al. Iron absorption by intestinal epithelial cells: CaCo2 cells cultivated in serum–free medium, on polyethyleneterephthalate microporous membranes, as an in vitro model. In Vitro Cellular and Development Biology. vol. 27A (1991) pp. 293–302.*

Chong et al., Evaluation of Biocoat® Intestinal Epithelium Differentiation Environment (3–Day Cultured Caco–2 Cells) as an Absorption Screening Model with Improved Productivity, Pharmaceutical Research, 1997, pp. 1835–1837, vol. 14, No. 12, Plenum Publishing Corporation.

Dehouck, et al., Drug Transfer Across the Blood–Brain Barrier: Correlation Between In Vitro and In Vivo Models, 1992, pp. 1790–1797, vol. 58, No. 5, Raven Press, Ltd., New York, J. Neurochem.

De Boer, et al., Multiparameter Analysis of Primary Epithelial Cultures Grown on Cyclopore Membranes, The Journal of Histochemistry and Cytochemistry, 1994, pp. 277–282, vol. 42, No. 2, The Histochemical Society, Inc., USA.

Halleux et al., Iron Absorption by Intestinal Epithelial Cells: 1. CaCo2 Cells Cultivated in Serum–Free Medium, on Polyethyleneterephthalate Microporous Membranes, as an In Vitro Model, In Vitro Cell. Deve. Biol., Apr. 1991, pp. 293–302, Tissue Culture Association.

Jarosch et al., Validation of a caco–2 cell monolayer culture for drug transport studies, Fourth International Conference on Drug Absorption, Edinburgh, Scotland Jun. 13–15, 1997, 10 pp.

* cited by examiner

METHODS FOR THE PREPARATION OF CELL MONOLAYERS

FIELD OF THE INVENTION

The present invention relates to cell based screens for studying drug transport. The invention also relates to improved methods for the preparation of cell monolayers for use in such screens.

DESCRIPTION OF RELATED ART

Cell based screens have increased in prominence during the last five years, particularly the use of human cell lines for studying drug transport. Cell lines are grown on permeable membrane supports to produce monolayers of cells which are used to examine drug transport via both absorptive and secretary processes. Current tissue culture methodologies for cells are laborious requiring extended culture periods (21 days post seeding onto filters) in order to obtain confluent monolayers of differentiated cells.

Streamlining of the current systems by reducing the time in culture is unsatisfactory since this leads to poor differentiation of the cells and poor expression of certain transporters which are important considerations for drug transport studies. Similarly, new methodology being introduced to reduce the culture time (e.g. Falcon BIOCOAT 3 day system) also results in sub-optimal monolayers in terms of functional expression of certain markers and relatively poor monolayer integrity as shown by the relatively high permeability of "impermeable" markers such as mannitol.

SUMMARY OF THE INVENTION

Our studies have now advantageously shown that it is possible to reduce time in culture dramatically but yet obtain differentiated cell monolayers in seven days or less.

Therefore according to a first aspect of the invention we provide a method for the preparation of a differentiated cell monolayer which methods comprises seeding a permeable charged polymeric support with confluent cells in an appropriate growth medium, incubating the support to allow cell attachment, and replacing the growth medium one or more times, whereby cells grown on the support and form a differentiated cell monolayer.

DETAILED DESCRIPTION OF THE INVENTION

The method of the invention may be used to prepare a cell monolayer of any convenient cell line. This is preferably a human cell line for use in studying drug transport. A particularly convenient cell line is the human adenocarcinoma cell line Caco-2, available from the European Collection of Animal Cell Cultures (ECACC 86010202) CAMR, Porton Down, Sailsbury, Wilshire, UK, SP4 0JG.

Figure 1:
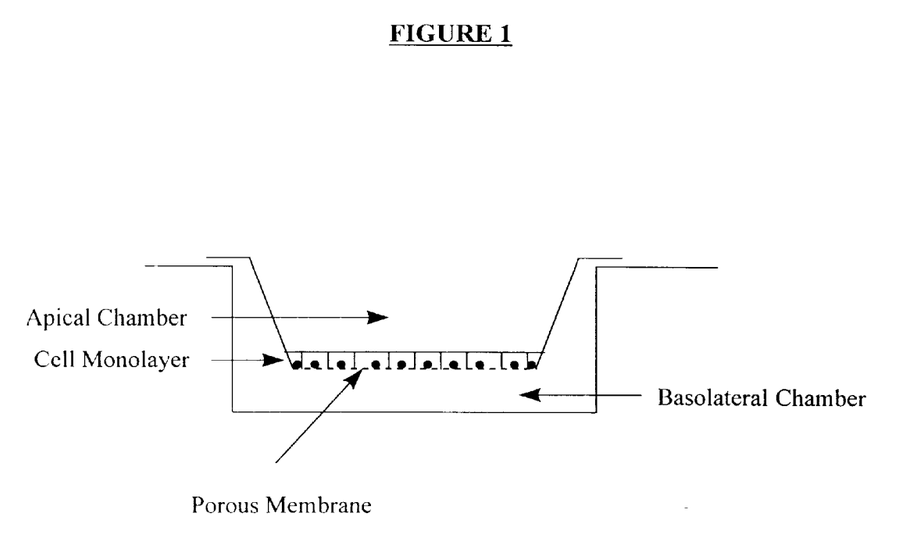
FIG. 1 shows a Caco-2 monolayer growing on a PET support in a cell culture plate insert

The permeable charged polymeric support is preferably collagen coated (to improve cell adhesion) and advantageously transparent. The support is preferably provided in the form of a filter and, for example, shaped to provide apical and basolateral chambers as shown in FIG. 1.

Therefore in a preferred aspect of the present invention we provide a method for the preparation of a differentiated monolayer of Caco-2 cells which method comprises seeding a permeable charged polymeric support with confluent Caco-2 cells in an appropriate growth medium, incubating the support to allow cell attachment, replacing the growth medium one or more times, whereby the Caco-2 cells grow on the support to form a differentiated Caco-2 cell monolayer.

This system takes a total of seven days with only one, preferably two replacements of the growth medium being necessary to produce satisfactory monolayers. When compared with the routinely used three week system, the process is more cost effective both in terms of reducing the materials used and minimising the degree of manual intervention involved which also helps to reduce the likelihood of contamination.

The growth medium is preferably replaced, in all chambers, about 24 hours after seeding the charged polymeric support for cell growth. This allows any excess cells to be removed. The growth medium is replaced again, about five days after seeding the charged polymeric support for cell growth. By this time the cell monolayer is ready for the preferred addition of a maturation agent as explained hereinafter.

The growth medium comprises any convenient energy and carbon source for the growing cells. A preferred source is L-glutamine, such as a 2 mM solution of L-glutamine, more preferably the more concentrated M1 serum-free supplement (Imperial Laboratories). The growth medium may also comprise one or more of the following: cell nutrients, vitamins, cofactors. Human transferrin is a further ingredient.

Antibiotics, such as penicillin and streptomycin, may be added to the growth medium to inhibit the growth of bacteria.

Monolayers produced have acceptable barrier properties for assessing passive permeability of drugs (based on restricted permeability of mannitol), and show functional expression of the dipeptide carrier and p-glycoprotein. The ability to produce viable Caco-2 cell monolayers within seven days also provides greater scope for applying the system early in drug candidate selection.

The permeable charged polymeric support is conveniently polyethylene terephthalate (PET), polycarbonate, cellulose acetate, cellulose nitrate, mixed polymer, preferably polyethylene terephthalate (PET). Whilst we do not wish to be bound by theoretical considerations, it is believed that a PET support allows better initial cell attachment and subsequent growth.

The M1 serum-free supplement used in this method contains a mixture of amino acids, vitamins, trace elements, other organic supplements and transferrin. It helps maintain viability of high density cultures when used in conjunction with media containing serum by providing a nutrient-rich supplement in a convenient form.

A further advantage is that a maturation agent can be used to good effect in the method of the invention. This helps to prevent leakiness between cell junctions and promotes an intact cell monolayer. In general the maturation agent is added about 5 days after seeding. Any convenient maturation agent may be used, preferred agents include butyric acid and sodium butyrate.

Not only does the method of the invention provide a more efficient process for preparation of integral confluent monolayers but also these monolayers have significantly improved membrane barrier properties (reduced mannitol permeability) and good expression of biochemical markers (alkaline phosphatase) compared to existing protocols.

By "a differentiated cell monolayer" we mean a cell monolayer that expresses a mature phenotype and is suitable for use in screens to study drug transport. In the case of Caco-2 cells, this may be characterised by one or more of the following features: a high density of microvilli on the apical surface, desmosomes, tight junctions as measured by permeability to mannitol ($P_{app}$ equivalent to <8×10$^{-7}$ cm/s and generally around 4×10$^{-7}$ cm/s), expression of a p-glycoprotein dipeptide transporter and reliable expression of differentiation markers such as alkaline phosphatase.

In a further aspect of the invention we provide differentiated cell monolayers prepared according to the methods of the invention.

Figure 2:
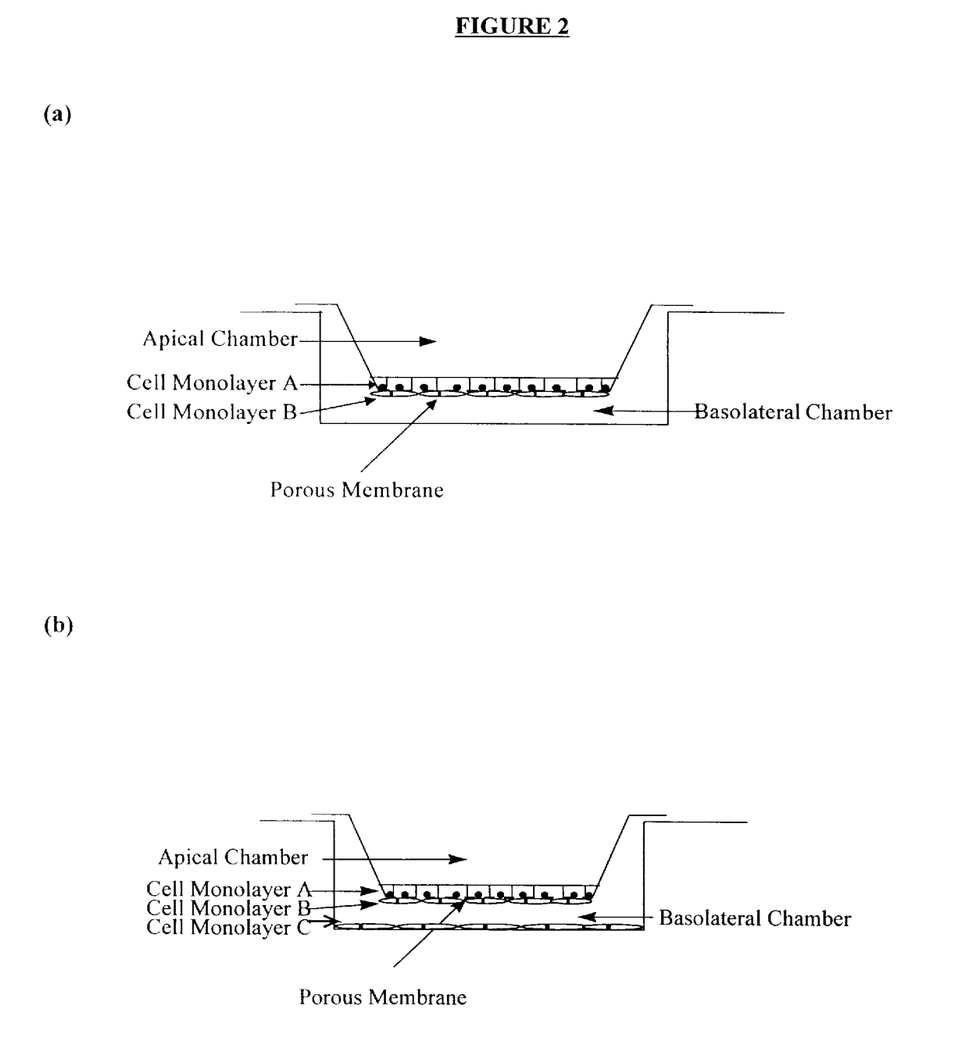
FIG. 2 shows cell monolayers growing on opposite sides of a PET support, (a) bi-layer culture and (b) bi-layer culture with target cell.

A further significant advantage is that the same or different cell monolayers may be grown on different surfaces of the charged polymeric support. Conveniently the cell monolayers may be grown on opposite surfaces for example opposite sides of the charged polymeric support. (e.g. Astrocytes/endothelial cells: endothelial cells/neuronal cells: hepatocytes/tumour epithelial cells etc.) In a preferred embodiment, two different cell monolayers are grown on opposite sides of a charged polymeric support to form a bilayer culture, for example as shown in FIG. 2a. In a further preferred embodiment, two different cell monolayers are grown on opposite sides of the charged polymeric support and a third target cell monolayer is grown in the culture dish to form a bilayer culture with target cell, for example as shown in FIG. 2b. Therefore in a further aspect of the invention we provide a permeable charged polymeric support having differentiated cell monolayers (which may be the same or different) on different surfaces of the support. It will be appreciated that the support may be provided in a number of shapes and will be limited only by practical considerations. Convenient shapes may include the following: disc, sphere, cylinder, cube, pyramid. In a preferred embodiment, the support comprises two opposite surfaces. The cell monolayers are advantageously different. It will be appreciated that two or more different cell monolayers may be grown on one particular surface of the charged polymeric support, or alternatively, two or more different cell monolayers may be grown on each of several different surfaces of the support. The same or different growth media may be used on opposite surfaces of the permeable charged polymeric support.

The differentiated cell monolayers of the invention can be used in any convenient screening procedure. These include procedures in any convenient format using any convenient number of individual wells, such as 6, 24 or 96 well formats. The number of wells is limited only by practical considerations.

Therefore in a further aspect of the present invention we provide the use of the differentiated cell monolayers of the present invention in screening methods to study drug transport.

The invention will now be illustrated but not limited by reference to the following Example and Figures:

EXAMPLE 1

Preparation of Intact Confluent Monolayers Using PET Filter Supports

Methods

Caco-2 cells are passaged weekly using trypsin/EDTA solution and are cultured in Growth Medium (see below)

Pre-wetting 3 ml Plating Medium (see below) is placed into each well of a 6-well plate. An insert is then introduced into each well at an angle so that air is allowed to escape from underneath the insert. The insert is then allowed to fall into position. 0.5 ml Plating Medium is added to the insert and swirled to ensure that the whole surface is wet. The plate is incubated at room temperature for a period of approximately 10 minutes. The volumes used in a 24 well plate were 400 μL in each apical chamber, and 1 mL in each basolateral chamber.

Caco-2 cells that have been grown for approximately 7 days are harvested by removing spent growth medium and discarding. The monolayer is washed with Hank's Balanced Salts Solution (HBSS) without $Ca^{++}$ & $Mg^{++}$ and the washings are discarded.

Cells are harvested enzymatically, typically using trypsin/EDTA solution which is added and evenly distributed around the whole of the cell sheet by rocking the flask. Any excess is then removed and discarded. The flasks are incubated for a period of approximately 3–4 minutes or until the cells detach from the flask with a gentle tap.

The cells are resuspended in Plating Medium and gently pipetted up and down to break up any large cell clumps.

Cells are counted using trypan blue and a haemocytometer, then diluted further in Plating Medium to give a final cell density of 1.5×10$^6$/ml.

1 ml of this suspension is then added to each 6 well insert and the plates are incubated at 37° C. in a humidified atmosphere of 5% $CO_2$ in air.

The following day the plates are media changed by aspirating the medium in the insert and the well and replacing with fresh Plating Medium (ensuring that no air bubbles become trapped beneath the insert).

Plates are then incubated for a further 4 days as above.

On day 5 from seeding the spent medium is discarded and replaced with Induction Medium (containing 1 mM Butyric Acid or Sodium Butyrate).

The plates are then incubated a further 48 hours prior to assay.

Materials

Caco-2 cells were obtained from ECACC 86010202 and used from our working bank. They are used in this model from passage 26 to 48. Stock cells are seeded at $5 \times 10^5$ cells per 175 $cm^2$ flask in 50 ml growth medium (or Plating Medium) and incubated for 7 days in 5% $CO_2$ in air prior to harvesting. Approximately $50 \times 10^6$ cells are obtained from each flask.

Growth Medium (stock cultures): DMEM (Life Technologies Cat No. 41966)+10% Fetal Calf Serum (LabTech Cat No. 4-101-500)+2 mM L-Glutamine*(Life Technologies Cat No. 25030)*10% M1 Serum-free substitute (Imperial Laboratories Cat. No.7-916) may be used instead of L-Glutamine.

Plating Medium: DMEM (Life Technolgies Cat No. 41966)+10% Fetal Calf Serum (LabTech Cat No. 4-101-500)+10% M1(Imperial Laboratories Cat. No.7-916)+1% Pen/Strep (Life Technologies Cat No. 15070).

Induction Medium: Plating Medium plus 1 mM Butyric Acid or 1 mM Sodium Butyrate (Sigma Chemical Company Cat No. B2503 or B5887 respectively)

Trypsin/EDTA solution: 1 ml of 2.5% Trypsin solution (Life Technologies Cat No. 25090) is added to 19 ml of 0.08% EDTA (Sigma cat No. EDS Free acid) in Ca/Mg-free Phosphate Buffered Saline (pH 7.3).

Hank's Balanced Salts Solution without Ca & Mg (Life Tech Cat No. 14170)

Inserts:6 well: Falcon Biocoat (Cat No. 40472) or PET (Cat No. 3102)1 $\mu$M pore size 24 well: Falcon PET (Cat No. 351181) 1 $\mu$M pore size Comments 24 hours after plating the cells into the inserts the centre of the insert will have many floating/dead cells which will be removed on changing the medium. A similar picture is observed 4 days later when changing into induction medium. Care should be taken not to agitate the plates as excessive movement of these dead cells may cause damage to the intact sheet below.

The cells should appear almost fully confluent 24 hours after plating and no holes in the cell sheet should be apparent when adding the induction medium.

Figure 3:
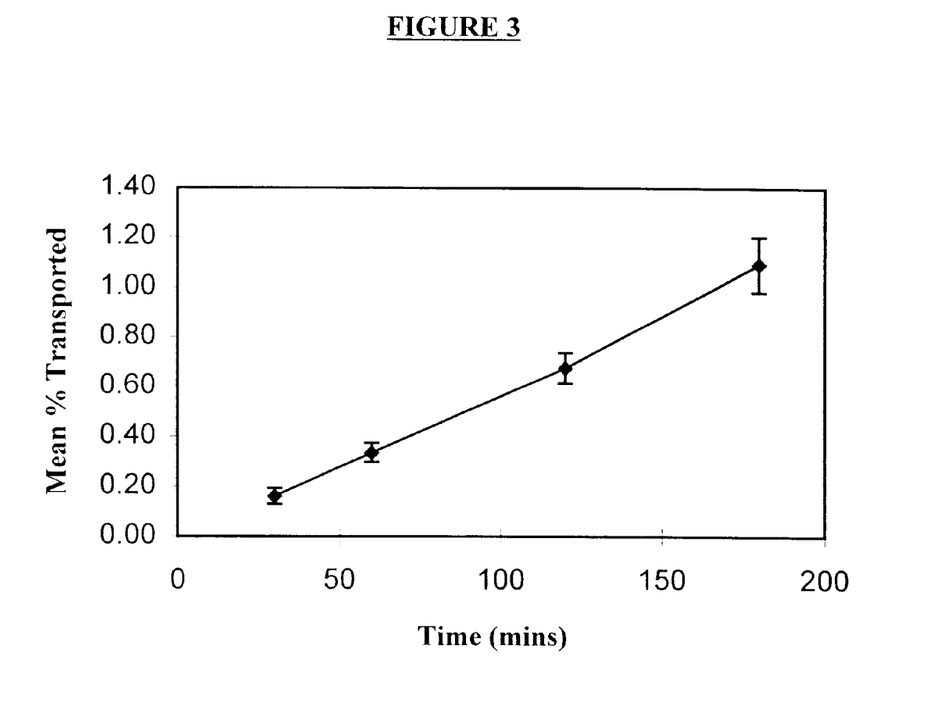
FIG. 3 shows the Average Mannitol Transported 0.36–0.40% over 60 minutes (cells cultured on 6well Biocoat inserts).
Figure 6:
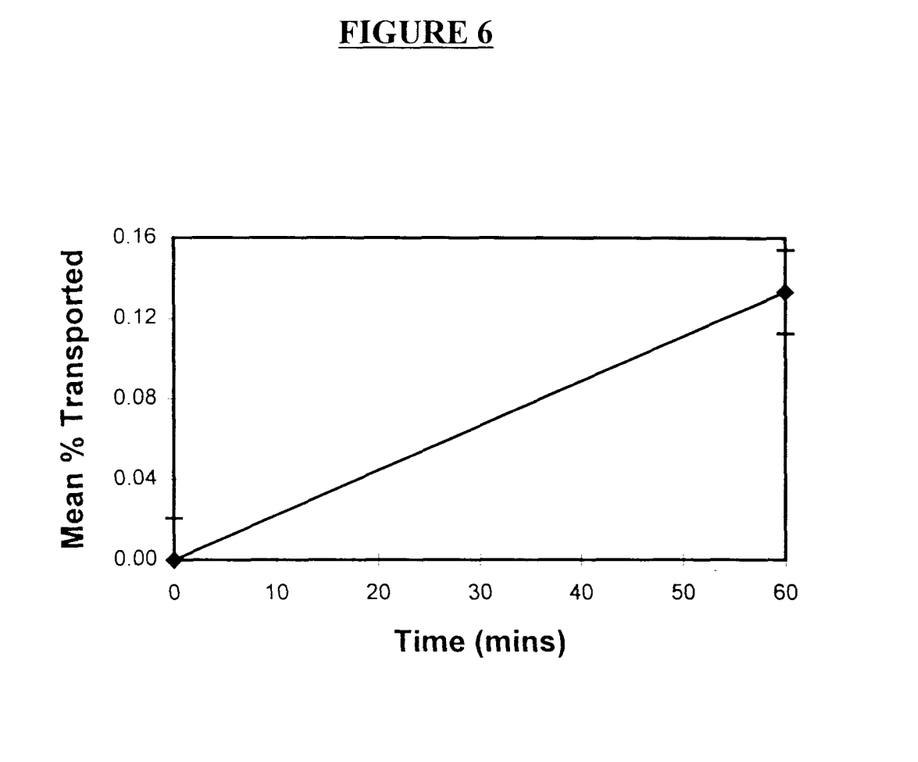
FIG. 6 shows the Average Lucifer Yellow Transported 0.13% over 60 minutes (cells cultured on 24well PET inserts).

Assessment of Confluency:

This was carried out with the hydrophilic markers, $^{14}$C-mannitol and Lucifer Yellow. The Average Mannitol Transported 0.36–0.40% over 60 minutes is shown in FIG. 3. The Average Lucifer Yellow Transported 0.13% over 60 minutes is shown in FIG. 6.

Comparison of Typical Mannitol Absorption Figures:

| SYSTEM | $P_{app}$(cm.s$^{-1}$ × 10$^6$) | % Transported/hour |
|---|---|---|
| Present Invention | 0.4 | <0.5 |
| BIOCOAT "3 day" system | <4.0 | |
| Polycarbonate (1) | 0.1–1.0 | 0.05 |
| Polycarbonate (2)* | 0.76 | |
| Polycarbonate (3) | | 1.5 |

* $^3$H-Mannitol (other figures given are for $^{14}$C-Mannitol which has a lower permeability than $^3$H-Mannitol)

(1) Artursson P et al "Studying Transport Process in Absorptive Epithelia" In:Cell Models of Epithelial Tissues A Practical Approach. Ed Shaw A, IRL, Oxford 1996.

(2) Duizer E et al J. Of Controlled Release 49 (1997) 39–49

(3) Taub M E Int. J. Of Pharmaceutics 156 (1997) 219–228

Comparison of Typical Lucifer Yellow Absorption Figures:

| SYSTEM | % Transported/hour |
|---|---|
| Present Invention | 0.13 |
| Polycarbonate (4) | 0.11 |

(4) Hidalgo I et al Gastroenterology 96 (1989) 736–749.

Assessment of Transporters:

The presence of both the apical di-peptide transporter and the secretory membrane transporter P-glycoprotein has been demonstrated by the present invention. Data for collagen coated 6 well(Biocoat) filters and 24 well PET filters are shown below.

Figure 4A:
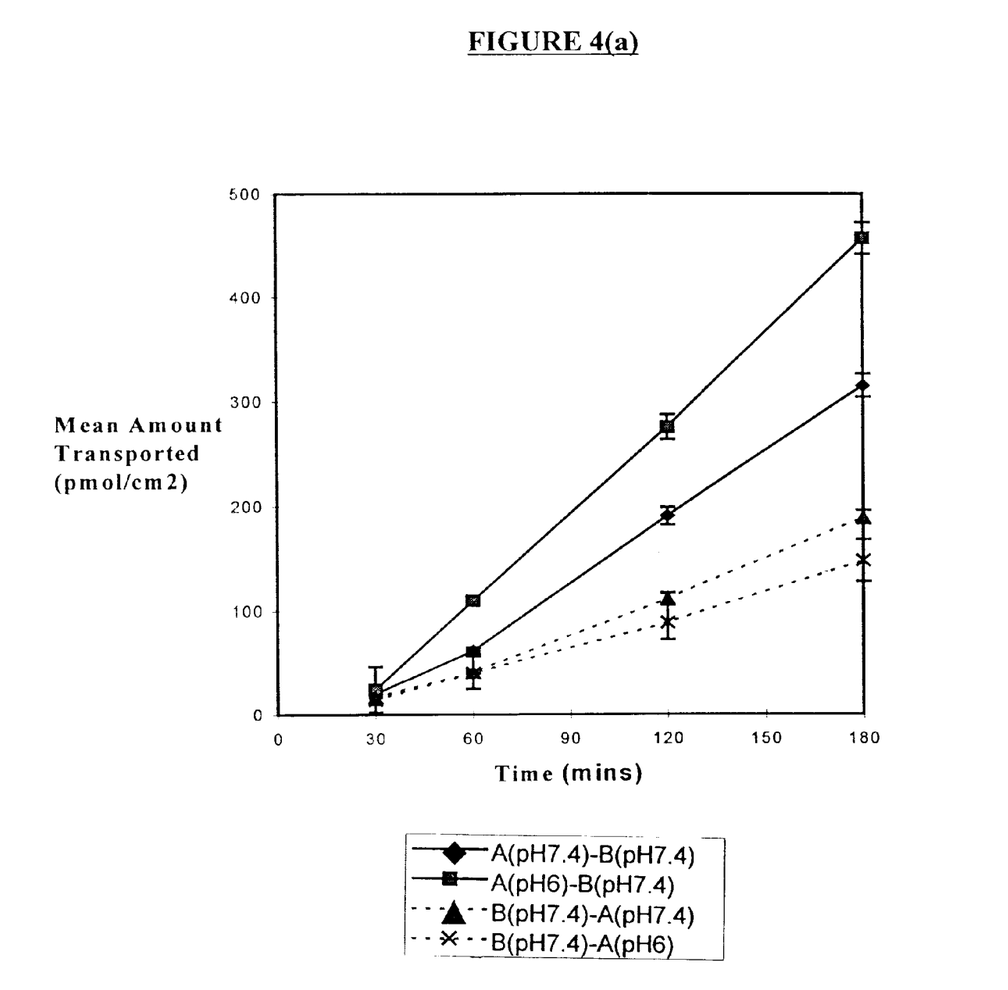
FIG. 4(a) shows the transport of $^{14}$C-Gly-sar across collagen coated filters in both the A-B and B-A directions at pH 6 and 7.4 (cells cultured on 6well Biocoat inserts). The increased transport in the A-B direction together with the pH dependency of transport demonstrates the presence of the apical di-peptide transporter within this invention.

FIG. 4(a) shows the transport of $^{14}$C-Gly-sar across collagen coated 6 well filters in both the A-B and B-A directions at pH 6 and 7.4. The increased transport in the A-B direction together with the pH dependency of transport demonstrates the presence of the di-peptide transporter within the invention.

Figure 4B:
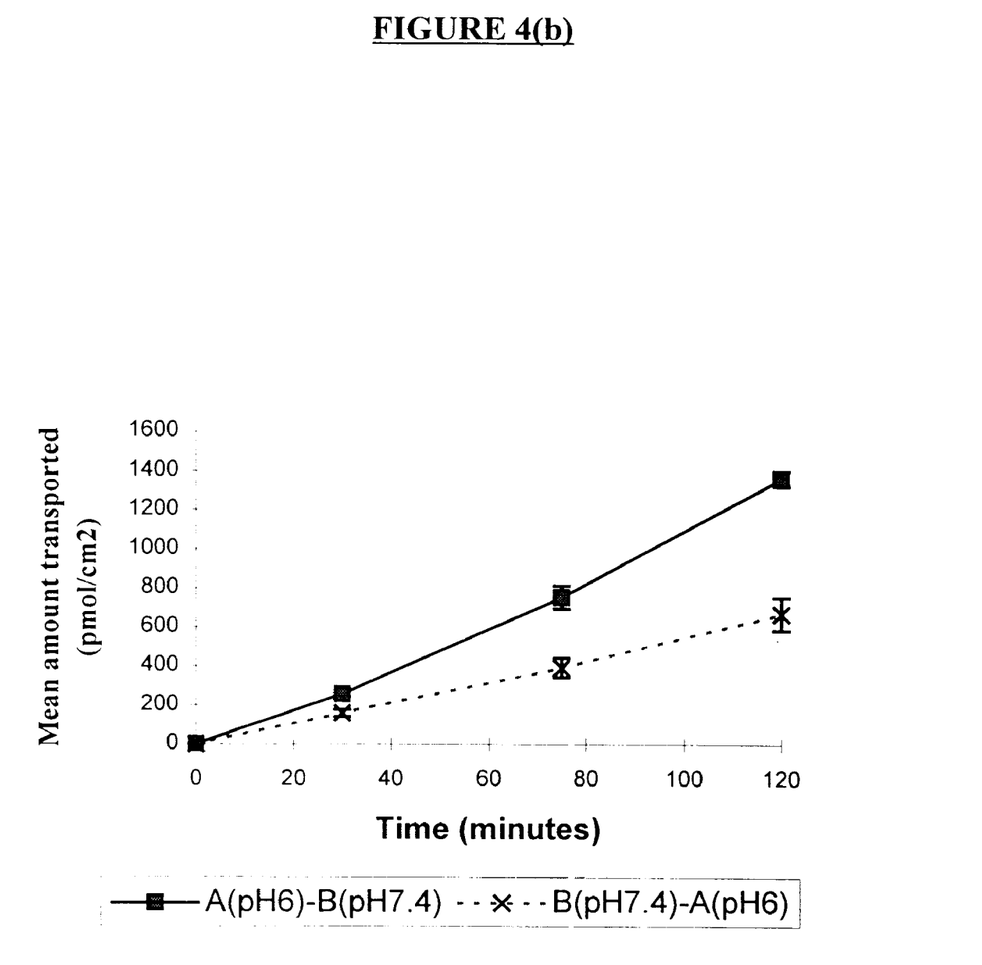
FIG. 4(b) shows the transport of $^{14}$C-Gly-sar across filters in both the A-B and B-A directions at pH 6 and 7.4 (cells cultured on 24well PET inserts). The increased transport in the A-B direction provides supportive evidence for the presence of the apical di-peptide transporter in a miniaturised system.
Figure 5:
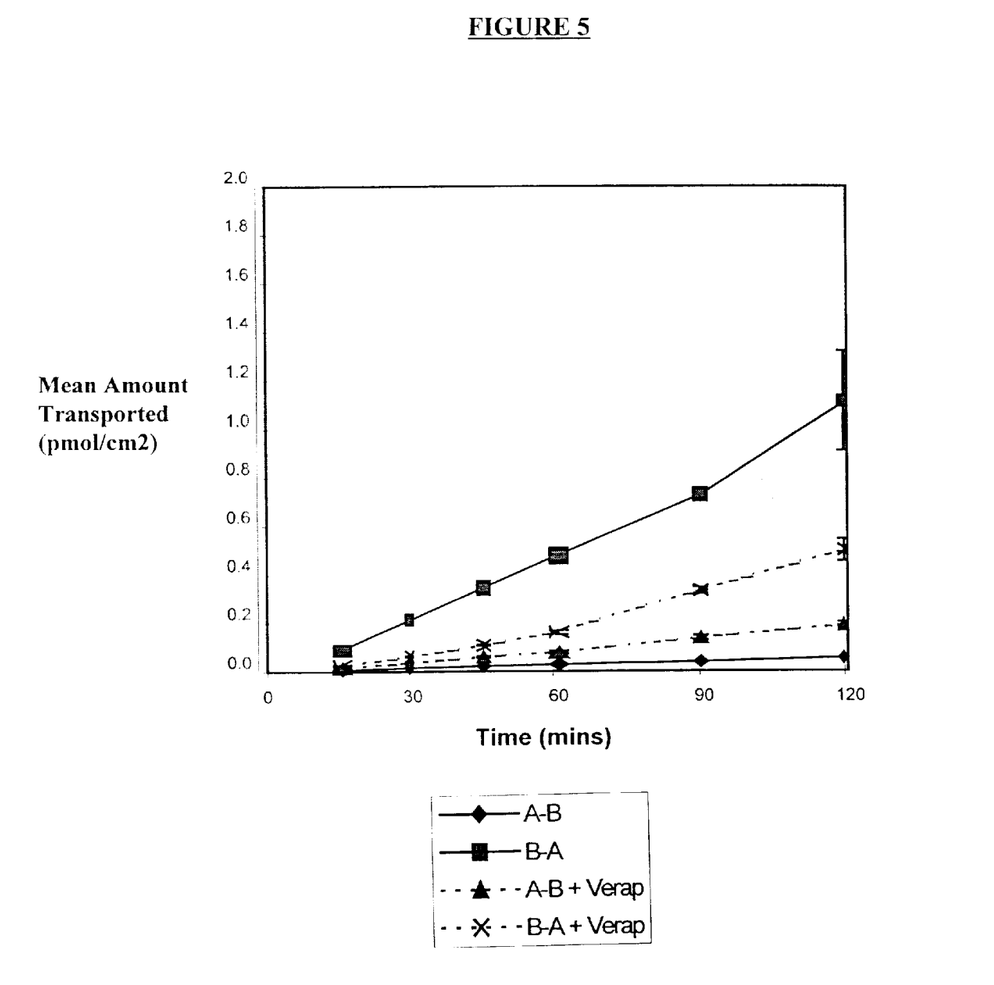
FIG. 5 shows transport in both the A-B and B-A directions of $^3$H-vinblastine, a known substrate for the secretory membrane transporter P-glycoprotein (cells cultured on 6 well Biocoat inserts). It illustrates the significantly greater B to A transport as compared to the A to B transport and the reduced transport in the secretory (B to A) direction and increased transport in the absorptive (A to B) in the presence of verapamil, a known inhibitor of the P-glycoprotein transporter.

FIG. 4(b) shows the transport of $^{14}$C-Gly-sar across 24 well filters in both the A-B and B-A directions at pH 6 and 7.4. The increased transport in the A-B direction provides supportive evidence for the presence of the apical di-peptide transporter in a miniaturised system.

Transport Experiments:

Solutions of drug for screening are prepared with Hank's Balanced Salts solution (HBSS) buffered to pH7.4 with HEPES. Up to 1% DMSO may be added to aid solubilisation. These drug solutions are added to either the apical (1.5 ml) or the basolateral (3.0 ml) chambers of a 6 well system, and HBSS at pH7.4 is added to the opposite chamber. 0.5 ml samples are taken at regular time intervals from the receiver chamber and the volume replaced with fresh pre-warmed HBSS at pH7.4. A donor sample is taken initially and at the final time point. Samples are analysed using appropriate methods. The volumes are modified accordingly for other plate formats (e.g. 400 $\mu$L apical volume, 1 mL basolateral volume for a 24 well plate).

The results are expressed as cumulative amount or percentage transported versus time. An absorption apparent permeability coefficient, $P_{app}$, can been calculated where:

$$P_{app}(\text{cm/s}) = \frac{dQ}{dt} \frac{1}{A \ C_0} \frac{1}{60}$$

where dQ/dt is the permeability rate (over the linear portion of the curve), $C_0$ is the initial concentration in the donor chamber and A ($cm^2$) is the surface area of the filter insert supporting the cell monolayer.

What is claimed is:

1. A method for preparation of a differentiated cell monolayer, useful for study of drug transport, which method comprises seeding a permeable, charged polymeric support with confluent cells of human adenocarcinoma cell line CaCo-2 in a growth medium, incubating the support to allow cell attachment, and replacing the growth medium about one day and again about 5 days after initial incubation, wherein a maturation agent is added to the growth medium about 5 days after seeding, whereby cells grow on the support and form a differentiated cell monolayer in about seven days, wherein said monolayer is characterized by permeability to mannitol in a range of about $4–8×10^{-7}$ cm/s.

2. A method as claimed in claim 1 wherein the permeable charged polymeric support is collagen coated.

3. A method as claimed in claim 1 wherein the permeable charged polymeric support is transparent.

4. A method as claimed in claim 1, wherein the permeable charged polymeric support is a filter.

5. A method as claimed in claim 1 wherein the growth medium comprises M1 serum-free supplement.

6. A method as claimed in claim 1 wherein the permeable charged polymeric support is polyethylene terephthalate.

7. A method as claimed in claim 1, wherein more than one cell monolayer is grown on different surfaces of the permeable charged polymeric support.

8. A method as claimed in claim 1 wherein the support comprises two opposite surfaces.

* * * * *